US010459347B2

(12) United States Patent
Boonzajer Flaes et al.

(10) Patent No.: US 10,459,347 B2
(45) Date of Patent: Oct. 29, 2019

(54) INSPECTION METHOD, INSPECTION APPARATUS AND ILLUMINATION METHOD AND APPARATUS

(71) Applicant: ASML Netherlands B.V., Veldhoven (NL)

(72) Inventors: Dirk Ewoud Boonzajer Flaes, Amsterdam (NL); Stefan Michiel Witte, Hoofddorp (NL); Kjeld Sijbrand Eduard Eikema, Hoofddorp (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/453,049

(22) Filed: Mar. 8, 2017

(65) Prior Publication Data

US 2017/0269482 A1    Sep. 21, 2017

(30) Foreign Application Priority Data

Mar. 15, 2016  (EP) ..................................... 16160277

(51) Int. Cl.
*G03F 7/20* (2006.01)
*G01B 11/00* (2006.01)
(Continued)

(52) U.S. Cl.
CPC ............ *G03F 7/7065* (2013.01); *G01B 11/00* (2013.01); *G01N 21/4788* (2013.01); *G01N 21/956* (2013.01); *G02B 21/16* (2013.01); *G03F 7/70625* (2013.01); *G03F 7/70633* (2013.01); *G01N 2201/061* (2013.01);
(Continued)

(58) Field of Classification Search
CPC .. G01B 11/00; G01N 21/4788; G01N 21/956; G01N 2201/061; G03F 7/7065
See application file for complete search history.

(56) References Cited

U.S. PATENT DOCUMENTS 7,792,246 B2   9/2010 Rodenburg et al.
8,908,910 B2  12/2014 Maiden
(Continued)

FOREIGN PATENT DOCUMENTS

WO    WO 2015/095621 A1    6/2015

OTHER PUBLICATIONS

Harada et al., "The Coherent EUV Scatterometry Microscope for Actinic Mask Inspection and Metrology," Photomask and Next-Generation Lithography Mask Technology XVIII, Proc. of SPIE, vol. 8081, 2011; pp. 80810K-1-80810K-9.
(Continued)

*Primary Examiner* — Michelle M Iacoletti
(74) *Attorney, Agent, or Firm* — Sterne, Kessler, Goldstein & Fox P.L.L.C.

(57) ABSTRACT

In an inspection apparatus, a target on the surface is illuminated with illuminating radiation that comprises first and second illuminating components. The illuminating components form one or more periodic illuminating patterns on the surface. A plurality of scattered radiation patterns formed by the illuminating radiation after scattering by the target is captured at a detector for a number of values of a controllable characteristic of at least one of the illuminating components. The captured radiation is then used to reconstruct data describing the target.

17 Claims, 9 Drawing Sheets

(51) Int. Cl.
G01N 21/47 (2006.01)
G01N 21/956 (2006.01)
G02B 21/16 (2006.01)
H05G 2/00 (2006.01)

(52) U.S. Cl.
CPC ..... G01N 2201/0635 (2013.01); H05G 2/003 (2013.01); H05G 2/008 (2013.01)

(56) References Cited

U.S. PATENT DOCUMENTS

| | | | |
|---|---|---|---|
| 8,917,393 | B2 | 12/2014 | Maiden |
| 8,942,449 | B2 | 1/2015 | Maiden |
| 9,029,745 | B2 | 5/2015 | Maiden |
| 2005/0052644 | A1 | 3/2005 | Lewis et al. |
| 2009/0263002 | A1* | 10/2009 | Cremer ................. B82Y 20/00 382/133 |
| 2010/0241396 | A1 | 9/2010 | Rodenburg |
| 2014/0139815 | A1* | 5/2014 | Amir ................. G01N 21/4788 355/67 |
| 2016/0061750 | A1 | 3/2016 | Den Boef et al. |

OTHER PUBLICATIONS

Dierolf et al., "Ptychography & Lensless X-ray Imaging," Euro Physics News, vol. 39, No. 1, 2008; pp. 22-24.
J.M. Rodenburg, "A simple model of holography and some enhanced resolution methods in electron microscopy," Ultramicroscopy, vol. 87, 2001; pp. 105-121.
Anonymous, "Ptychography," Wikipedia, retrieved from https://en.wikipedia.org/wiki/Ptychography, last updated 2015; 2 pages.
Zurch M.W., "High-Resolution Extreme Ultraviolet Microscopy: Imaging of Artificial and Biological Specimens with Laser-Driven Ultrafast XUV Sources," Springer Theses, 2015; 139 pages.
Claus et al., "Ptychography: A novel phase retrieval technique, advantages and its application," International Conference on Applications of Optics and Photonics, Proc. of SPIE, vol. 8001, 800109; 2011; pp. 1-6.
McNulty I., "Coherence and partial coherence—what do we need?," Center for Nanoscale Materials, Argonne National Laboratory, MBA Lattice Workshop, Advanced Photon Source, Oct. 21-22, 2013; 14 pages.
Quiney H., "Partial coherence in diffractive X-ray imaging: towards biomolecular structure determination," ARC Centre for Coherant X-ray Science, European XFEL Seminar, Feb. 3, 2012; 56 pages.
Whitehead et al., "Diffractive Imaging Using Partially Coherent X Rays," The American Physical Society, Physical Review Letters, PRL 103, 243902, 2009; pp. 1-4.
International Search Report and Written Opinion of the International Searching Authority directed to International application No. PCT/EP2017/054476, dated Jun. 28, 2017; 15 pages.
Frohn et al., "True optical resolution beyond the Rayleigh limit achieved by standing wave illumination," PNAS, vol. 97, No. 13, Jun. 20, 2000; pp. 7232-7236.
Liu et al., "Phase retrieval in x-ray imaging based on using structured illumination," The American Physical Society, Physical Review A 78, Aug. 11, 2008; pp. 023817-1 to 023817-5.
Neil et al., "Real time 3D fluorescence microscopy by two beam interference illumination," Elsevier Science B.V., Optics Communications 153, Jul. 15, 1998; pp. 1-4.
Saxena et al., "Structured illumination microscopy," OSA, Advances in Optics and Photonics 7, May 26, 2015; pp. 241-275.

* cited by examiner

INSPECTION METHOD, INSPECTION APPARATUS AND ILLUMINATION METHOD AND APPARATUS

FIELD

The present invention relates to inspection apparatus and methods usable for acquiring data describing target structures. For example, the apparatus and methods are usable in the manufacture of devices by lithographic techniques. The apparatus and methods are also usable to acquire data describing non-periodic targets, such as biological structures or samples. The invention further relates to an illumination system for use in such apparatus and to methods of manufacturing devices using lithographic techniques. The invention yet further relates to computer program products for use in implementing such methods

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field.

However, the dimensions of modern product structures are so small that they cannot be imaged by optical metrology techniques at visible wavelengths. Small features include for example those formed by multiple patterning processes, and/or pitch-multiplication. While scanning electron microscopy (SEM) is able to resolve these modern product structures directly, SEM is much more time consuming than optical measurements.

Similar challenges occur when imaging biological structures, such as cells at micron or sub-micron resolutions. The ability to image biological structures is essential for studying cellular structure and function. Imaging plays a central role in medical diagnostics, being the gold standard in pathology for the identification of many diseases from biopsy samples.

Optical microscopy is a standard method for life science imaging, as the achievable resolution allows a detailed view of intracellular structures, while the field of view can be sufficiently large to image larger structures such as cellular networks and tissue specimen. A particular advantage of visible/near-infrared light microscopy is the low interaction of the light with cells (i.e. low absorption), so that biological material can be imaged without being influenced significantly by the light itself, while the light can be detected with high efficiency so that low intensity can be used.

Since cells are very transparent to light, image contrast in pathology is typically provided by staining cells with substances that absorb specific parts of the optical spectrum, leading to colored absorption contrast.

The inventor has considered whether the techniques of coherent diffraction imaging (CDI), combined with radiation of wavelength comparable with the product structures of interest, might be applied to defect detection on modern device structures. CDI is also known as lensless imaging, because there is no need for physical lenses or mirrors to focus an image of an object. The desired image is calculated synthetically from a captured light field. Various techniques for CDI are described in the PhD thesis describing lensless imaging at EUV wavelengths is "High-Resolution Extreme Ultraviolet Microscopy" by M. W. Zürch, Springer Theses, DOI 10.1007/978-3-319-12388-2_1. A particular type of CDI is ptychography, described for example in published patent application US 2010241396 and U.S. Pat. Nos. 7,792,246, 8,908,910, 8,917,393, 8,942,449, 9,029,745 of the company Phase Focus Limited and the University of Sheffield. D. Claus et al provide an introduction to ptychography in a paper "Ptychography: a novel phase retrieval technique, advantages and its application" Proc. SPIE 8001, International Conference on Applications of Optics and Photonics, 800109 (Jul. 26, 2011); doi:10.1117/12.893512. In ptychography, phase information is retrieved from a plurality of captured images with an illumination field that is moved slightly between successive captures. Overlap between the illumination fields allows reconstruction of phase information and 3-D images. Other types of CDI can be considered also.

Successful use of ptychography requires a number of requirements to be met. Firstly, the size of the radiation spot used to illuminate the target must be controlled very precisely in order to only illuminate part of a target. This is typically done by using optical elements with a high Numerical Aperture (NA). However, this can be both challenging and costly, in particular for radiation at extreme ultra-violet (EUV) wavelengths. Alternatively, it is possible to use a small aperture. This, however, leads to a large loss in radiation flux, which is undesirable. In particular, as described above, biological material is imaged at low radiation intensities to avoid the material being influenced by the radiation. A large loss in radiation flux may render such methods unfeasible for biological imaging purposes.

A second requirement is that the transverse displacement of the radiation beam relative to the target needs to be accurately known and controlled. This requires the relative position of the optical system and the target to be precisely controlled. This increases the complexity and cost of the system. It may further increase the physical space requirements of the system, which is undesirable.

As an alternative to the use of a finite radiation spot, structured illumination patterns have been proposed. However, in particular for radiation with EUV wavelengths, this requires the production of multiple coherent radiation patterns with small feature sizes. In turn, this requires the use of optical components which must be carefully positioned and maintained.

SUMMARY

According to a first aspect of the present invention, there is provided a method for acquiring data describing a target on a surface, the method comprising:

(i) providing illuminating radiation, wherein the illuminating radiation comprises at least one illuminating radiation beam, and wherein each of the at least one illuminating radiation beams comprises a first illuminating component and a second illuminating component, at least one of each of the first illuminating component or second illuminating component having a controllable characteristic;

(ii) illuminating a target with the at least one illuminating radiation beams such that each first illuminating component and each corresponding second illuminating component form a periodic illuminating pattern;

(iii) capturing at least one scattered radiation pattern formed by the illuminating radiation after scattering by the target for at least one value of the controllable characteristic; and reconstructing data describing the target based on the at least one scattered pattern.

The reconstructed data may for example be used to reconstruct an image of the target. In this manner, the present invention enables robust image reconstruction from a set of interference pattern illuminations of a target. Modifying an interference pattern, e.g. changing the phase of the pattern, can be achieved by using active components such as electro-optic modulators or fiber phase shifters. In other terms, there is no need for mechanical movement of the target, the radiation source or any of optical components in the radiation path. This enables faster and easier data acquisition than other implementations of ptychography, which typically use mechanically actuated mechanisms, such as sample/substrate stage scanning or radiation beam steering. In a lithographic process, reducing the measurement time directly increases the productivity of the lithographic system. Similarly, for purposes of imaging biological structures, the reduced complexity and increased robustness of the system greatly increases the utility of the system.

In some embodiments, the illuminating radiation may comprise a first illuminating radiation beam, the second illuminating component of said beam having a controllable characteristic, and the method may further comprise repeating steps (i)-(iii) for each of a plurality of values of the controllable characteristic.

In some embodiments, the illuminating radiation may comprise a plurality of illuminating radiation beams, the first illuminating component and the second illuminating component of each illuminating radiation beam having a controllable characteristic, and each of the plurality of illuminating radiation beams may correspond to a particular value of the controllable characteristic.

According to a second aspect of the invention, there is provided a method for illuminating a target on a surface, the method comprising:

illuminating the target on the surface with illuminating radiation, wherein the illuminating radiation comprises at least one illuminating radiation beam, the illuminating radiation beam comprising a first illuminating component and a second illuminating component, wherein each first illuminating component and each corresponding second illuminating component form a periodic illuminating pattern on the surface, and wherein at least one of each of the first and second illuminating components has a controllable characteristic; and controlling the value of the controllable characteristic of each of the at least one first and second illuminating components.

The invention further provides an illumination apparatus comprising means for carrying out the method as set forth above.

The invention yet further provides an inspection apparatus comprising for carrying out the method as set forth above.

The invention yet further provides a lithographic apparatus comprising an inspection apparatus as set forth above.

The invention yet further provides a method of manufacturing devices wherein device features and metrology targets are formed on a series of substrates by a lithographic process, wherein properties of the metrology targets on one or more processed substrates are measured by a method as set forth above, and wherein the measured properties are used to adjust parameters of the lithographic process for the processing of further substrates.

The invention yet further provides a computer program product containing one or more sequences of machine-readable instructions for implementing reconstructing or controlling steps in a method according to the invention as set forth above.

The invention yet further provides a lithographic system comprising:

a lithographic apparatus comprising an illumination optical system arranged to illuminate a pattern, and a projection optical system arranged to project an image of the pattern onto a substrate; and an inspection apparatus as set forth above, wherein the lithographic apparatus is arranged to use one or more parameters calculated by the inspection apparatus in applying the pattern to further substrates.

Further aspects, features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Before describing embodiments of the invention in detail, it is instructive to present an example environment in which embodiments of the present invention may be implemented.

Figure 1:
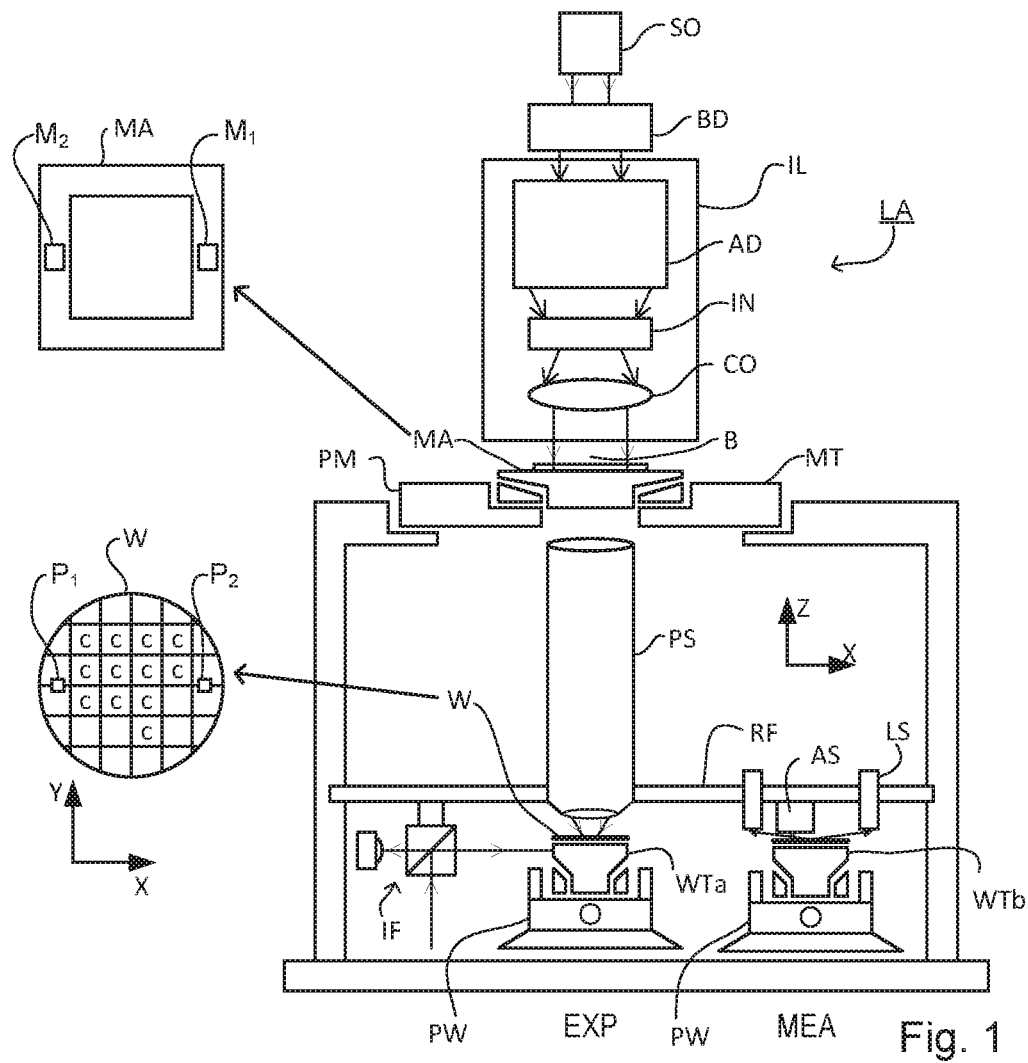
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; two substrate tables (e.g., a wafer table) WTa and WTb each constructed to hold a substrate (e.g., a resist coated wafer) W and each connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W. A reference frame RF connects the various components, and serves as a reference for setting and measuring positions of the patterning device and substrate and of features on them.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support MT may be a frame or a table, for example, which may be fixed or movable as required. The patterning device support may ensure that the patterning device is at a desired position, for example with respect to the projection system.

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

As here depicted, the apparatus is of a transmissive type (e.g., employing a transmissive patterning device). Alternatively, the apparatus may be of a reflective type (e.g., employing a programmable mirror array of a type as referred to above, or employing a reflective mask). Examples of patterning devices include masks, programmable mirror arrays, and programmable LCD panels. Any use of the terms "reticle" or "mask" herein may be considered synonymous with the more general term "patterning device." The term "patterning device" can also be interpreted as referring to a device storing in digital form pattern information for use in controlling such a programmable patterning device.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems.

In operation, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may for example include an adjuster AD for adjusting the angular intensity distribution of the radiation beam, an integrator IN and a condenser CO. The illuminator may be used to condition the radiation beam, to have a desired uniformity and intensity distribution in its cross section.

The radiation beam B is incident on the patterning device MA, which is held on the patterning device support MT, and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa or WTb can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment mark may also be included within dies, in amongst the device features, in which case it is desirable that the markers be as small as possible and not require any different imaging or process conditions than adjacent features. The alignment system, which detects the alignment markers is described further below.

The depicted apparatus could be used in a variety of modes. In a scan mode, the patterning device support (e.g., mask table) MT and the substrate table WT are scanned synchronously while a pattern imparted to the radiation beam is projected onto a target portion C (i.e., a single dynamic exposure). The speed and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, as is well-known in the art. For example, a step mode is known. In so-called "maskless" lithography, a programmable patterning device is held stationary but with a changing pattern, and the substrate table WT is moved or scanned.

Combinations and/or variations on the above described modes of use or entirely different modes of use may also be employed.

Lithographic apparatus LA is of a so-called dual stage type which has two substrate tables WTa, WTb and two stations—an exposure station EXP and a measurement station MEA—between which the substrate tables can be exchanged. While one substrate on one substrate table is being exposed at the exposure station, another substrate can be loaded onto the other substrate table at the measurement station and various preparatory steps carried out. This enables a substantial increase in the throughput of the apparatus. The preparatory steps may include mapping the surface height contours of the substrate using a level sensor LS and measuring the position of alignment markers on the substrate using an alignment sensor AS. If the position sensor IF is not capable of measuring the position of the substrate table while it is at the measurement station as well as at the exposure station, a second position sensor may be provided to enable the positions of the substrate table to be tracked at both stations, relative to reference frame RF. Other arrangements are known and usable instead of the dual-stage arrangement shown. For example, other lithographic apparatuses are known in which a substrate table and a measurement table are provided. These are docked together when performing preparatory measurements, and then undocked while the substrate table undergoes exposure.

Figure 2:
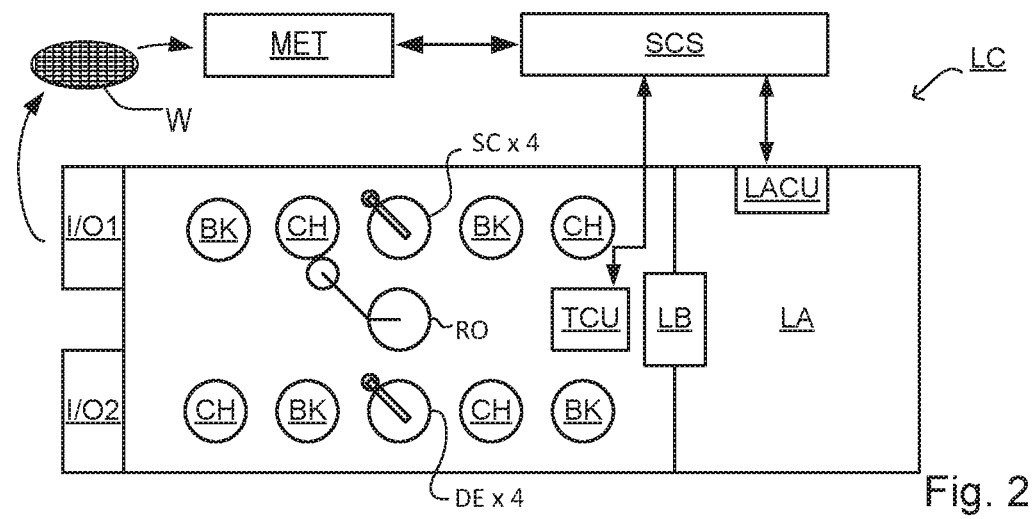
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency. The substrates processed by the track are then transferred to other processing tools for etching and other chemical or physical treatments within the device manufacturing process.

The lithographic apparatus control unit LACU controls all the movements and measurements of the various actuators and sensors described. LACU also includes signal processing and data processing capacity to implement desired calculations relevant to the operation of the apparatus. In the terminology of the introduction and claims, the combination of these processing and control functions referred to simply as the "controller". In practice, control unit LACU will be realized as a system of many sub-units, each handling the real-time data acquisition, processing and control of a subsystem or component within the apparatus. For example, one processing subsystem may be dedicated to servo control of the substrate positioner PW. Separate units may even handle coarse and fine actuators, or different axes. Another unit might be dedicated to the readout of the position sensor IF. Overall control of the apparatus may be controlled by a central processing unit, communicating with these subsystems processing units, with operators and with other apparatuses involved in the lithographic manufacturing process.

Figure 3:
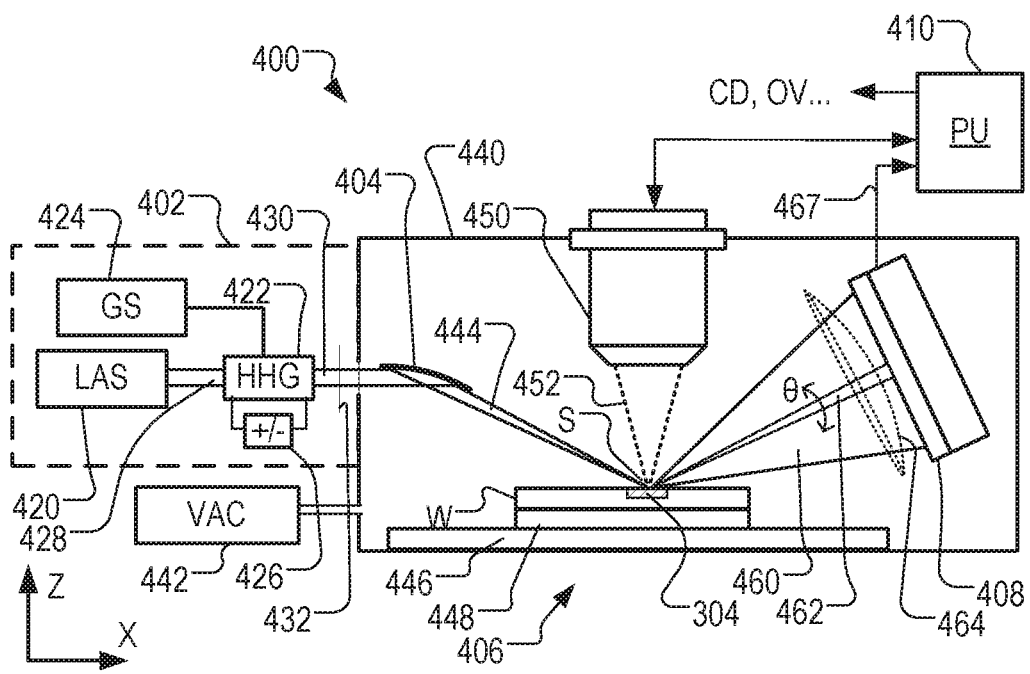
FIG. 3 illustrates schematically an inspection apparatus for use in measuring defects in a semiconductor product structure.

FIG. 3 illustrates in schematic form an inspection apparatus 400 for use in the metrology system MET of FIG. 2. This apparatus is for implementing so-called lensless imaging in wavelengths in the extreme UV (EUV) and soft x-ray (SXR) ranges. For example the radiation used may be at a selected wavelength or wavelengths less than 50 nm, optionally less than 20 nm, or even less than 5 nm or less than 2 nm.

Inspection apparatus 400 comprises an EUV radiation source 402, illumination optical system 404, substrate support 406, detector 408 and processor 410. Source 402 comprises for example a generator of EUV radiation based on high harmonic generation (HHG) techniques. Such sources are available for example from KMLabs, Boulder Colo., USA (http://www.kmlabs.com/). Main components of the radiation source are a pump laser 420 and an HHG gas cell 422. A gas supply 424 supplies suitable gas to the gas cell, where it is optionally ionized by electric source 426. The pump laser may be for example a fiber-based laser with an optical amplifier, producing pulses of infrared radiation lasting less than 1 ns (1 nanosecond) per pulse, with a pulse repetition rate up to several megahertz, as required. Typical pulse durations may be in the sub-picosecond range. The wavelength may be for example in the region of 1 μm (1 micron). The laser pulses are delivered as a first beam of radiation 428 to the HHG gas cell 422, where a portion of the radiation is converted to higher frequencies. The filtered radiation beam 430 includes coherent radiation of the desired EUV wavelength or wavelengths. The radiation for the purpose of coherent diffraction imaging should be spatially coherent but it may contain multiple wavelengths. If the radiation is also monochromatic the lensless imaging calculations may be simplified, but it is easier with HHG to produce radiation with several wavelengths. These are matters of design choice, and may even be selectable options within the same apparatus. One or more filtering devices 432 may be provided. For example a filter such as a thin membrane of Aluminum (Al) may serve to cut the fundamental IR radiation from passing further into the inspection apparatus. A grating may be provided to select one or more specific harmonic wavelengths from among those generated in the gas cell. Some or all of the radiation path may be contained within a vacuum environment, bearing in mind that the desired EUV radiation is absorbed when traveling in air. The various components of radiation source 402 and illumination optics 404 can be adjustable to implement different metrology 'recipes' within the same apparatus. For example different wavelengths and/or polarization can be made selectable.

For high-volume manufacturing applications, selection of a suitable source will be guided by cost and hardware size, not only by theoretical ability, and HHG sources are selected as the example here. Other types of sources are also available or under development that may be applied in principle. Examples are synchrotron sources, FEL (free electron laser) sources and filtered plasma-based sources. T. Depending on the materials of the structure under inspection, different wavelengths may offer a desired level of penetration into lower layers, for imaging of buried structures. For example, wavelengths above 4 or 5 nm may be used. Wavelengths above 12 nm may be used, as these show stronger penetration specifically through silicon material and are available from bright, compact HHG sources. For example, wavelengths in the range 12 to 16 nm may be used. Alternatively or in addition, shorter wavelengths may be used that also exhibit good penetration. For example, wavelengths shorter than 2 nm may be used, as and when a practical source becomes available. Wavelengths in ranges above 0.1 nm and below 50 nm might therefore be considered, including for example the range 1 to 2 nm. The apparatus may be a stand-alone device or incorporated in either the lithographic apparatus LA, or the lithographic cell LC. It can also be integrated in other apparatuses of the lithographic manufacturing facility, such as an etching tool. The apparatus may of course be used in conjunction with other apparatuses such as scatterometers and SEM apparatus, as part of a larger metrology system.

From the radiation source 402, the filtered radiation beam 430 enters an inspection chamber 440 where the substrate W including a product structure is held for inspection by substrate support 406. The product structure is labeled 304, indicating that he apparatus is particularly adapted for metrology on non-periodic structures, such as the logic area 304 of the product shown in FIG. 3. The atmosphere within inspection chamber 440 is maintained near vacuum by vacuum pump 442, so that EUV radiation can pass without undue attenuation through the atmosphere. The Illumination optics 404 has the function of focusing the filtered radiation beam 430 into a focused beam of illuminating radiation 444, and may comprise for example a two-dimensionally curved mirror, or a series of one-dimensionally curved mirrors. The focusing is performed to achieve a round spot roughly 10 μm in diameter, when projected onto the product structure. Substrate support 406 comprises for example an X-Y translation stage 446 and a rotation stage 448, by which any part of the substrate W can be brought to the focal point of the beam of illuminating radiation 444 in a desired orientation. Thus the radiation spot S is formed on the structure of interest. Tilting of the substrate in one or more dimensions may also be provided. To aid the alignment and focusing of the spot S with desired product structures, auxiliary optics 450 uses auxiliary radiation 452 under control of processor.

Detector 408 captured radiation 460 that is scattered by the product structure 304 over a range of angles θ in two dimensions. A specular ray 462 represents a "straight through" portion of the radiation. This specular ray may optionally be blocked by a stop (not shown), or pass through an aperture in detector 408. In a practical implementation, images with and without the central stop may be taken and combined to obtain a high dynamic range (HDR) image of a diffraction pattern. The range of angles of diffraction can be plotted on a notional sphere 464, known in the art as the Ewald sphere, while the surface of the detector 408 will more conveniently be flat. Detector 408 may be for example a CCD image detector comprising an array of pixels.

Figure 4:
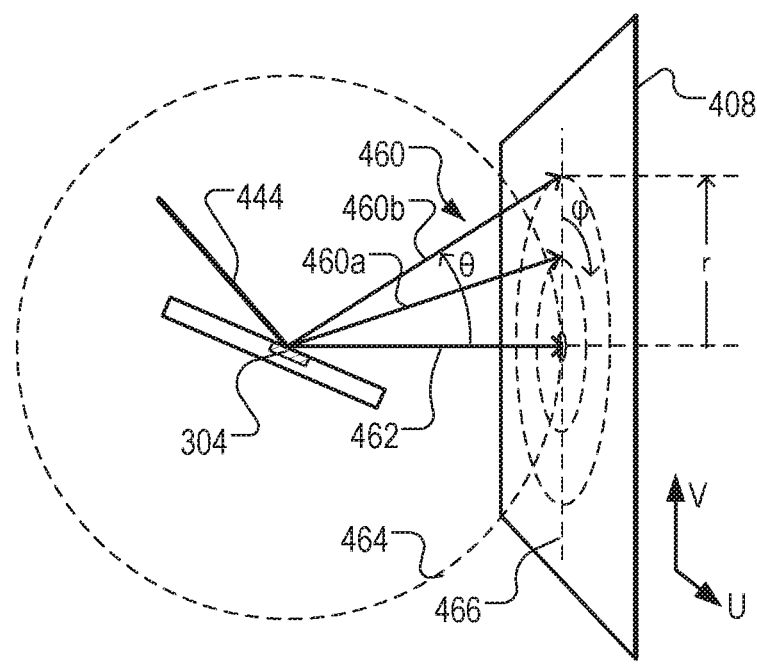
FIG. 4 (not to scale) illustrates the mapping of diffraction angles to pixels on a planar detector in the apparatus of FIG. 3.

FIG. 4 (not to scale) illustrates the mapping of diffraction angles (and consequently points on the Ewald sphere 464) to pixels on a planar detector 408. The dimensions of the pixel array are labeled U, V in a pseudo-perspective representation. The diffracted radiation 460 is deflected by a sample product structure at a point that defines the center of the Ewald sphere 464. Two rays 460a and 460b of the diffracted radiation are scattered by the product structure, with respective angles θ relative to the specular ray 462. Each ray 460a, 460b passes through a point on the (notional) Ewald sphere impinges on a particular point in the (actual) U-V plane of detector 408, where it is detected by a corresponding pixel detector. Knowing the geometry of the apparatus within the inspection chamber, processor 410 is able to map pixel positions in an image captured by detector 408 to angular positions on the Ewald sphere 462. For convenience, the specular portion 462 of the reflected radiation is aligned with the horizontal direction in the diagram, and a direction normal to the plane of detector 408, but any coordinate system can be chosen. Thus a radial distance r on detector 408 can be mapped to an angle θ. A second angular coordinate φ represents deflection out of the plane of the diagram, and can be mapped also from the position on the detector. Only rays with φ=0 are shown in this illustration, corresponding to pixels on a line 466 on the detector.

Returning to FIG. 3, pixel data 467 is transferred from detector 408 to processor 410. Using lensless imaging, a 3-D image (model) of the target can be reconstructed from the diffraction pattern captured on the image detector. From the reconstructed image, measurements of deviations such as overlay and CD are calculated by processor 410 and delivered to the operator and control systems of the lithographic manufacturing facility. Note that the processor 410 could in principle be remote from the optical hardware and inspection chamber. Functions of the processor could be divided between local and remote processing units, without departing from the principles disclosed herein. For example, a local processor may control the apparatus to capture images from one or more product structures on one or more substrates, while a remote processor processes the pixel data to obtain measurements of the structure. The same processor or yet another processor could form part of the supervisory control system SCS or lithographic apparatus controller LACU and use the measurements to improve performance on future substrates.

As mentioned, the inspection apparatus is arranged to perform coherent diffraction imaging (CDI). Various techniques for CDI are described in the PhD thesis describing lensless imaging at EUV wavelengths is "High-Resolution Extreme Ultraviolet Microscopy" by M. W. Zürch, Springer Theses, DOI 10.1007/978-3-319-12388-2_1.

Referring to FIG. 5, a particular type of CDI is ptychography, described for example in published patent application US 2010241396 and U.S. Pat. Nos. 7,792,246, 8,908,910, 8,917,393, 8,942,449, 9,029,745 of the company Phase Focus Limited and the University of Sheffield. D. Claus et al provide an introduction to ptychography in a paper "Ptychography: a novel phase retrieval technique, advantages and its application" Proc. SPIE 8001, International Conference on Applications of Optics and Photonics, 800109 (Jul. 26, 2011); doi:10.1117/12.893512. In ptychography, phase information is retrieved from a plurality of captured images with an illumination field that is moved slightly between successive captures. Overlap between the illumination fields allows reconstruction of phase information and 3-D images. Other types of CDI can be considered also.

Figure 5A:
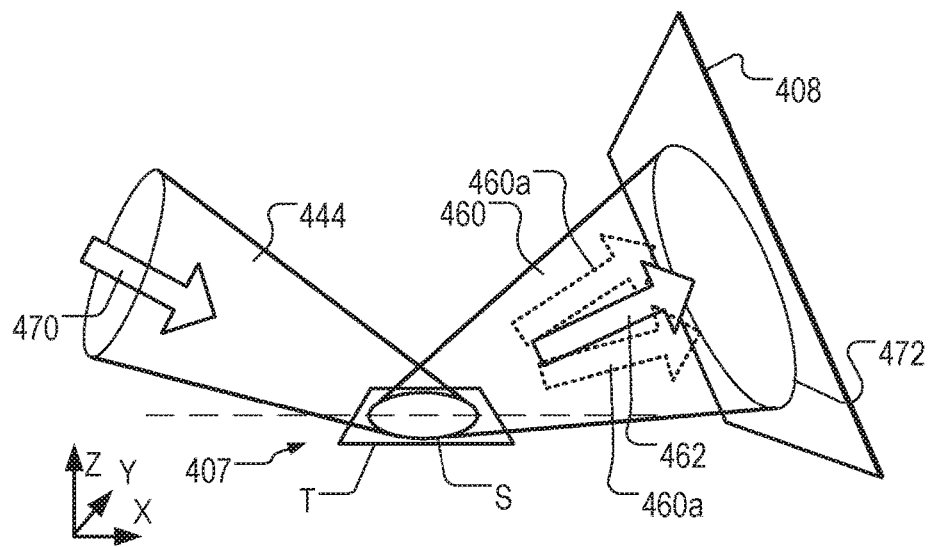
FIGS. 5(a)-5(c) illustrate obtaining of diffraction patterns from overlapping portions of a target structure for performing ptychography with the apparatus of FIG. 3.

In FIG. 5(a), we see the incident beam 444, the scattered beam 460 and the detector 408 during capture of one image of the diffraction pattern. The structure of interest 407 is represented by a square target area T. The focused spot S is at a first position, for example in the middle of the target area. Incident rays 470 are represented, specular rays 462 and scattered rays 460a, 460b, corresponding to the like-numbered rays in FIG. 6. It will be appreciated that these rays are only representative, and within the beams 444 and 460 rays are spread over a range of angles of incidence and scattering. From each point within the spot S, specular rays 462 are incident at all points within area 472 on the detector. Scattered rays 460a, 460b similarly can be incident at any point on the detector. Consequently, as explained in the Claus et al paper, diffraction orders of structures of interest within the spot S overlap with one another to form the diffraction pattern captured by detector 408. The radiation in beam 444 is spatially coherent, within the spot area S.

While full spatial coherence across the spot area would simplify calculations, it is found that partial coherence can be sufficient for good diffraction imaging, provided additional steps are applied in calculations. A survey of research in his area is provided in the presentation "Coherence and partial coherence—what do we need?" by Ian McNulty, Center for Nanoscale Materials, Argonne National Laboratory, USA, at the MBA Lattice Workshop, Advanced Photon Source, 21-22 Oct. 2013 (retrieved from the Internet 11 Aug. 2015). These and further techniques are reviewed in a presentation "Partial coherence in diffractive X-ray imaging: towards biomolecular structure determination" by Harry Quiney, ARC Centre for Coherent X-ray Science, School of Physics, The University of Melbourne (retrieved from Internet 11 Aug. 2015). In one such technique, the partially coherent radiation is modeled as superposition of a few spatially coherent modes. CDI can be performed by optimizing for each mode individually providing for these modes individually within the CDI algorithm, rather than trying to treat the radiation as coherent. This technique is described further in "Diffractive Imaging Using Partially Coherent X Rays" by L. W. Whitehead et al, Phys. Rev. Lett. 103, 243902 (2009), the contents of which are incorporated herein by reference.

Figure 5B:
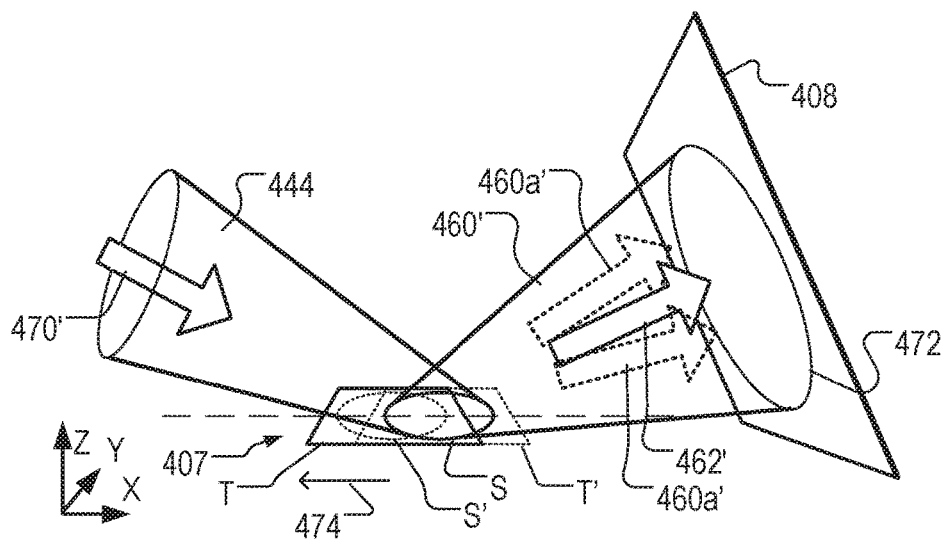

At FIG. 5(b) we see the capturing of a second diffraction pattern. At least two patterns are required for ptychography. The process is identical to that shown in FIG. 7(a). A small displacement 474 (in this illustration a translation in the X direction) has been made between the substrate and the incident beam which is now labeled 444'. As mentioned, the apparatus can record such displacement very accurately using sensors 456. Details of the displacement 474 are recorded, along with the captured diffraction patterns. In a practical implementation, adapted for use in semiconductor manufacturing, the source and other optical components will likely remain stationary, while the substrate with target are T moves to a new position using stages 446, 448 under control of processor 410. In principle, the structure of interest could remain stationary while the other components move. The spot S now falls on target area T with a spot area different from, but significantly overlapping the former position S'. The former position of target area T is shown as T'. Scattered rays 460a', 460b' are captured on detector 408 as before. The diffraction pattern, which records only intensity, may be very similar to that captured in FIG. 5(a), but slight differences between the patterns can be used to reconstruct phase information, thanks to the overlapping of the spot areas S and S'. The degree of overlap between adjacent spot areas may be greater than 30%, for example around 50% of the spot area.

Figure 5C:
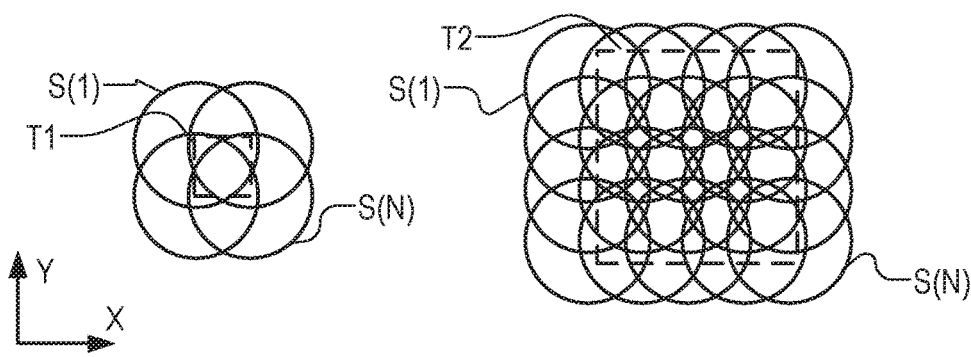

More than two diffraction patterns may be captured, as required. FIG. 5(c) shows two examples where a target areas T1 and T2 are each covered by a series of displaced radiation spots S(1) to S(N), all mutually displaced in X and/or Y directions but all overlapping significantly one or more of their neighbors. Bearing in mind that even though the spot S is only 5 or 10 μm in diameter, the resolution of imaging desired is on the order of 1 nm. The area that is covered by the calculated image corresponds to those areas where at least two spots overlap, so the rectangular areas T1, T2 could in principle be extended into a more complex shape if desired. Nevertheless, it will be appreciated that the synthesized image might cover a target area T1 that is only for example 2 μm by 2 μm, in the case of area T1. Even so, it may encompass many hundreds or even thousands of functional devices within a product. Consequently, only two or a few captures may be required in a practical inspection task.

Successful use of the above-described inspection apparatus requires careful control of the radiation spot size as well as the relative positioning between the target and the illumination optical system. As previously described, and in particular for radiation at EUV wavelengths, this requires additional optical elements in the illumination optical system, which is both challenging and costly. Alternatively, a small aperture may be used. However, this leads to a significant portion of the illuminating radiation being blocked, which is undesirable since it increases the loss of radiation flux. Additionally, the transverse displacement of the radiation beam relative to the target needs to be accurately known and controlled. This requires the relative position of the optical system and the target to be precisely controlled.

A known alternative to the use of a finite radiation spot size is the use of structured illumination patterns. However, in particular for radiation with EUV wavelengths, this requires the production of multiple coherent radiation patterns with small feature sizes. In turn, this requires the use of optical components which must be carefully positioned and maintained. Yet other alternatives involve the use of a spatial light modulator or adaptive optical projection devices.

Figure 6A:
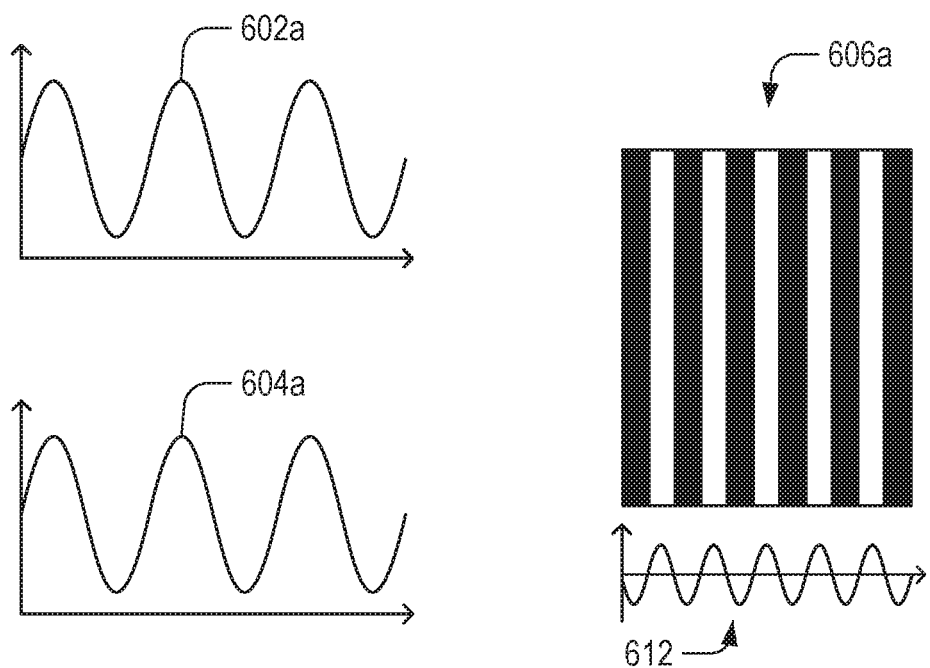
FIGS. 6(a)-6(b) illustrate the principle of a method for providing illuminating radiation according to the present invention.
Figure 6B:
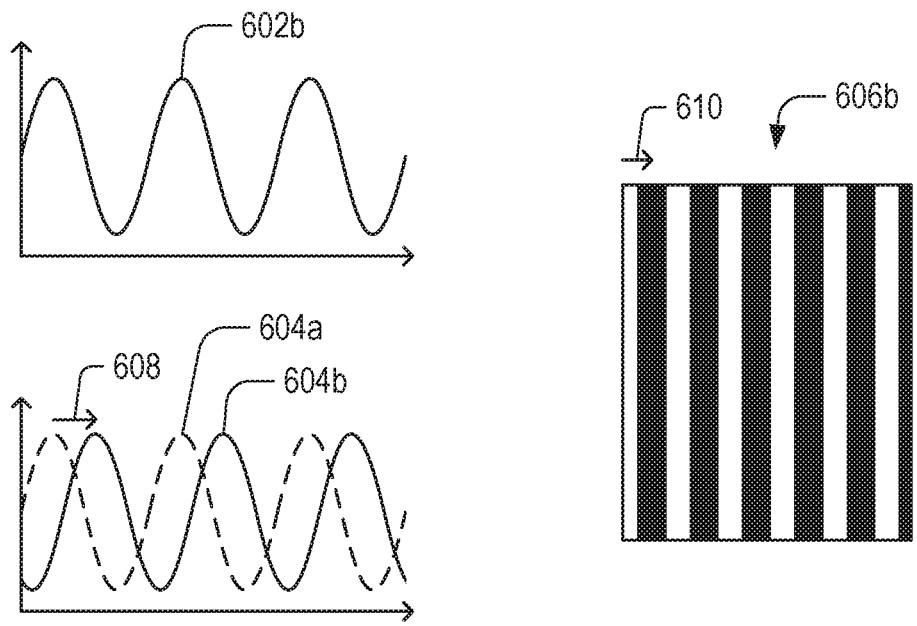

The inventors have realized that it is possible to overcome or mitigate at least some of the above disadvantages by using illumination patterns with a one-dimensional periodic amplitude modulation. Such illumination patterns can be produced without requiring the use of a complicated, and therefore expensive, illumination optical system. FIGS. 6(a) and 6(b) show an exemplary principle of creating structured illumination that may be used in the examples discussed in the following.

FIG. 6(a) shows a first wave 602a and a second wave 604a. The second wave is substantially identical to the first wave, i.e. the first and second waves have a constant phase difference and an identical wavelength. In other terms, the second wave is coherent with the first wave. More specifically, the first and second waves are what is known in the art as "temporally coherent". It is, however, to be noted that while temporal coherence is described in the present example, other types of coherence could, in principle, equally well be used.

As the first wave and the second wave are coherent, they can be directed towards a surface where they will form a periodic illuminating pattern. The pattern is caused by the interference of the first wave with the second wave. The pattern will, in the following, be referred to interchangeably as "periodic illuminating pattern" and "interference pattern". An exemplary interference pattern 606 is shown in FIG. 6(a). The exemplary interference pattern comprises a number of parallel stripes or lines alternating between dark and light. It will of course be noted that the interference pattern 606a is formed by two coherent radiation beams that interfere on a surface, wherein both of the beams have a non-perpendicular incidence angle with the surface. This interference pattern is used for exemplary purposes only and is not intended to have a limiting effect. It will also be realized that, while shown in FIG. 6(a) as a binary pattern, this is for illustrative purposes only, and that the variation between light and dark areas may in reality be described by a non-binary function (such as a sinusoidal function 612 below interference pattern 606a).

FIG. 6(b) illustrates a situation where the phase of the second wave 604b is changed relative to the phase of the first wave 604a. In effect, changing the phase of a wave is equivalent to moving the waveform along the x-axis, as indicated by the arrow 608. For reference, the original second wave 604a is indicated by the dashed line.

The shift in phase of the second wave 604b causes the interference pattern 606b to spatially translate horizontally, as indicated by arrow 610, while leaving the period of the pattern unchanged.

The example shown in FIG. 6 has a number of advantages when compared with known ptychography measurements. Rather than physically translating the target with respect to the illumination optical system, the interference pattern is spatially translated by merely by controlling one or more controllable characteristics of the radiation. As previously described, this obviates the need for an actuating mechanism, which may be both complex and expensive to make. Additionally, physical translation of a target is slower than changing a characteristic of the radiation.

Additionally, the size of the radiation spot does not need to be limited, which reduces or obviates the need for additional components to control the radiation spot, thereby reducing the loss of radiation flux. Since the radiation spot size enables a larger target area to be covered, fewer images are required for a single target reconstruction.

It will be appreciated that the first and second waves need only be coherent during a measurement period. Since the measurement period can be shorter, and since fewer images need to be recorded, compared with the known ptychography measurements, the control requirements for the illuminating radiation are much less stringent. This further reduces the complexity and cost of the inspection apparatus.

It will of course also be appreciated that the above is exemplary only, and that several different ways of implementing a translation of the interference pattern may be envisaged by the skilled person.

Figure 7:
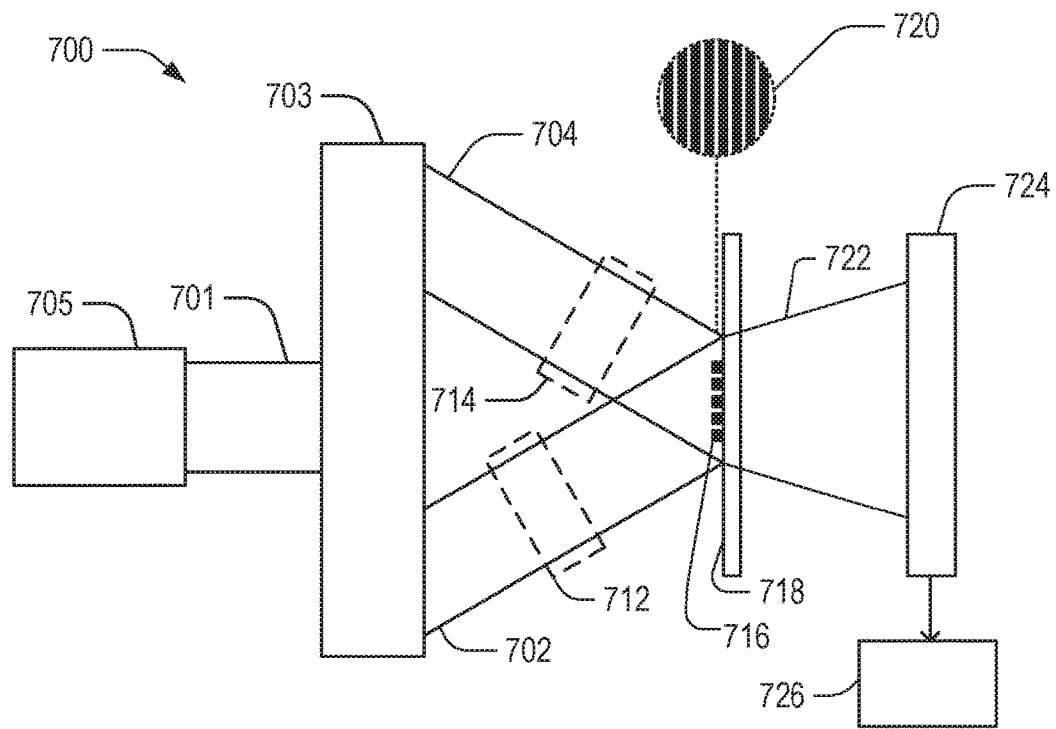
FIG. 7 shows an inspection apparatus according to a first embodiment of the invention.
Figure 8:
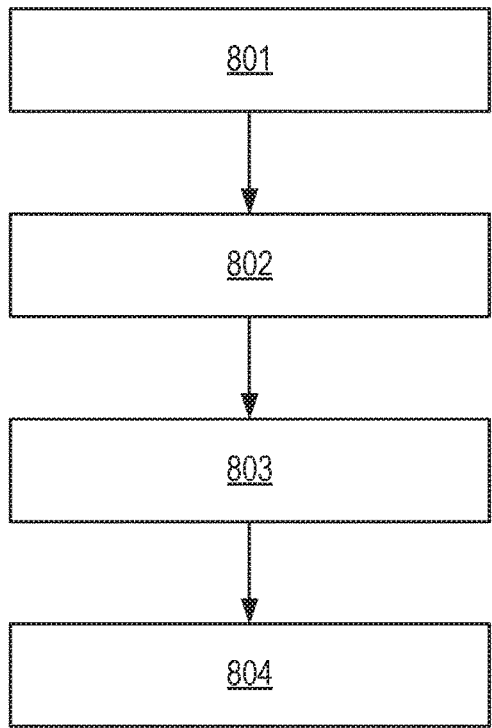
FIG. 8 illustrates a method for using the inspection apparatus of FIG. 7.

FIGS. 7 and 8 illustrate an exemplary apparatus and corresponding method for acquiring an image of a target on a surface. In the present example, the target is depicted as a periodic target located on a surface. Periodic targets are commonly placed on substrates used in lithographic processes and are used for making measurements during the lithographic processes. However, it is to be noted that the method and apparatus described in example of FIGS. 7 and 8, as well as any of the examples described subsequently, may equally well be used with non-periodic targets. For example, as described above, the method and apparatus may be used to image biological structures, such as cells or pathological samples.

In a first step 801, illuminating radiation is provided. The illuminating radiation comprises at least one illuminating radiation beam 701. The one or more illuminating radiation beams is typically emitted by a radiation source 705. It will of course be noted that the radiation source can comprise one or more specific radiation generators. In one example, the radiation source comprises a single laser source emitting an illuminating radiation beam, for example having a central wavelength in the visible spectrum. In another example, the radiation source comprises a plurality of individual laser sources whose output beams are combined to form the illuminating radiation beam in a suitable manner. In a specific example, the illuminating radiation beam comprises a plurality of central wavelengths within the visible spectrum. The one or more illuminating radiation beams is split into a first illuminating component 702 and a second illuminating component 704 by a beamsplitting system 703. The illuminating radiation beam(s) may be split in any suitable fashion. In one example the illuminating radiation beam(s) may be split by a single beamsplitter. In other examples, the beamsplitting system comprises a plurality of optical components.

It will of course be appreciated that, while the radiation source is exemplified by one or more laser sources emitting radiation with a visible wavelength in the above, any suitable radiation source with any desired or suitable wavelength output range may, in principle, be used. For example, radiation sources emitting radiation in the infrared spectrum, ultra-violet spectrum (e.g., having a wavelength of or about 365, 355, 248, 193, 157 or 126 nm) or in the EUV spectrum (e.g., having a wavelength in the range of 5-20 nm) can equally well be used.

It should be noted that, although an "illuminating beam" may be referred to, it is not, in principle, necessary that the first illuminating component and the second illuminating component originate from a single radiation source. It is, in principle, possible for the first illuminating component and the second illuminating component to be provided by separate radiation sources, as long as the coherence requirement between the first illuminating component 702 and the second illuminating component 704 is met. As discussed above, this requirement is fulfilled as long as the first illuminating component is coherent with the second illuminating component during the measurement process. If the coherence requirement is met, the first and second illuminating components can be considered to originate from a single beam.

At least one of each of the first illuminating component or second illuminating component has a controllable characteristic. It will, of course, be appreciated that a plurality of exemplary implementations may be envisaged. In an example, wherein the illuminating radiation comprises a single illuminating radiation beam, one of the first illuminating component or the second illuminating component comprises a controllable characteristic. In another example, the illuminating radiation comprises a plurality of illuminating radiation beams, wherein each of the first and second illuminating components comprise a controllable characteristic.

Examples of controllable characteristics include, but are not limited to, wavelength, phase, angle of incidence on the surface, or the optical path length of the one or more illuminating components.

Each of the first illuminating component and the second illuminating component may optionally propagate through additional optical components 712, 714. While omitted here for purposes of clarity, the apparatus 700 may comprise such additional components, e.g. for controlling the first and second illuminating components.

In a second step 802, a target 716 positioned on a surface 718 is illuminated with the at least one illuminating radiation beam, such that each of the first illuminating components (exemplified by 702) and the second illuminating components (exemplified by 704) form a periodic illuminating pattern 720 (as described with reference to FIG. 5).

In a third step 803, at least one scattered radiation pattern 722 formed by the illuminating radiation after scattering by the target is captured at a detector 724 for at least one value of the controllable characteristic. While the detector is shown in FIG. 7 as receiving radiation transmitted through the target and the surface, it will be appreciated that this is exemplary only. The detector can equally well be positioned so as to receive radiation that is reflected by the target rather than transmitted through the target and the surface (as illustrated in FIG. 3).

In a fourth method step 804, data describing the target is reconstructed based on the data relating to the at least one scattered radiation patterns obtained by the detector. The data may be reconstructed by a processing unit 726 to which the data obtained by the detector is transmitted. In some embodiments, the data may comprise "image data" from which an image of the target may be reconstructed. The processing unit may be a dedicated processing unit provided in the inspection apparatus. Alternatively, the processing unit may form part of the lithographic apparatus control unit (LACU), or it may be a remotely located processing unit connected to the inspection apparatus.

A further exemplary apparatus and method for acquiring an image of a periodic target on a surface will now be described with reference to FIGS. 9 and 10. For ease of comparison with FIGS. 7 and 8, elements of FIGS. 9 and 10 similar to corresponding elements of FIGS. 7 and 8 are labelled with reference signs similar to those used in FIGS. 7 and 8, but with prefixes "9" and "10" instead of "7" and "8". Additionally, for sake of conciseness and clarity, only the parts of FIGS. 9 and 10 that differ from the corresponding parts of FIGS. 7 and 8 will be described in detail in the following.

In a first step 1001, illuminating radiation is provided that comprises at least one illuminating radiation beam 901 emitted by a radiation source 905. The illuminating radiation beam is split into a first illuminating component 902 and a second illuminating component 904 by a beam splitting system 903.

Figure 9:
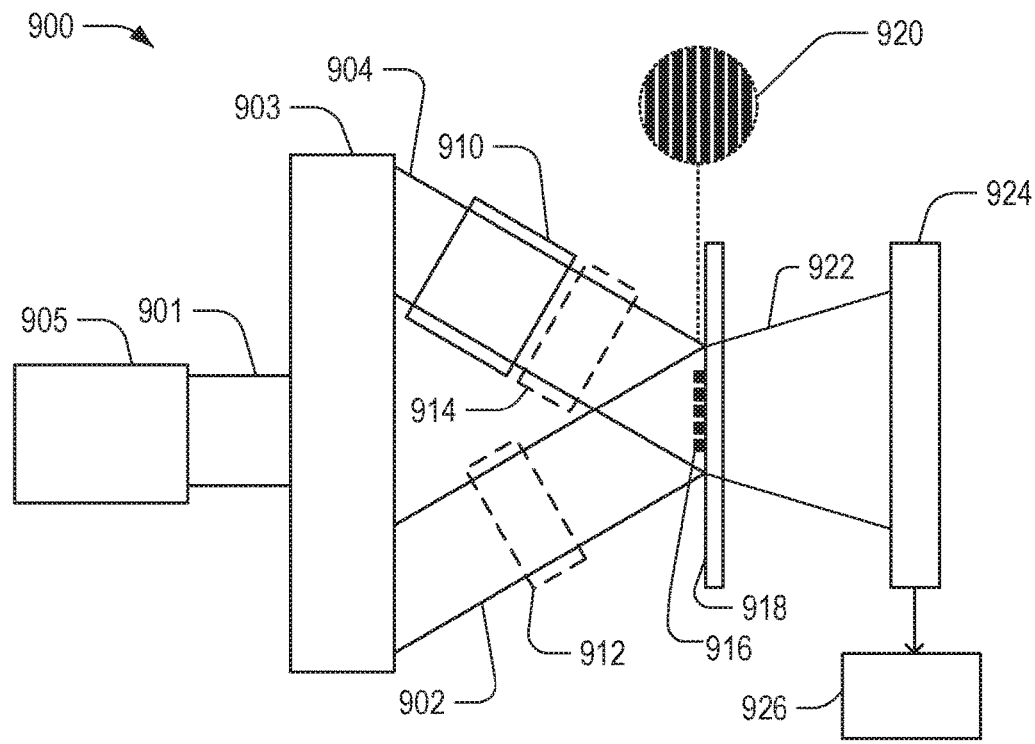
FIG. 9 shows an inspection apparatus according to a second embodiment of the invention.

As discussed above, it should be noted that the apparatus shown in FIG. 9 is exemplary only, and that a number of specific implementations may be readily envisaged by the skilled person. In an example, the apparatus comprises two separate radiation sources; a first radiation source that provides the first illuminating component, and a second radiation source that provides the second illuminating component, the first and second illuminating components being mutually coherent.

In a second step 1002, a target 916 positioned on a surface 918 is illuminated such that each of the first illuminating components (exemplified by 902) and the second illuminating components (exemplified by 904) form a periodic illuminating pattern 920.

In a third step 1003, at least one scattered radiation pattern 922 formed by the illuminating radiation after scattering by the target is captured at a detector 924 for at least one value of the controllable characteristic.

It will be noted that steps 1001-1003 are substantially identical to steps 801-803 of the method discussed with reference to FIG. 8.

The first to third method steps 1001-1003 are repeated for a plurality of different values of the controllable characteristic (as indicated by the arrow 1005). In one example, methods steps 1001-1003 may be repeated for a plurality of different phases of the second illuminating component. In another example, method steps 1001-1003 may be repeated for a plurality of optical path lengths for the second illuminating component. In yet another example, method steps 1001-1003 may be repeated for a plurality of angles of incidence of the second illuminating component on the surface of the surface.

In order to ensure sufficient accuracy of the result of the following method step, method steps 1001-1003 will typically be repeated more than a minimum required number of times. A typical number of repetitions may be between 3 and 20, and more preferably between 5 and 15. Yet more preferably, the number of repetitions may be 10.

In a fourth method step 1004, data describing the target is reconstructed based on the data relating to the at least one captured patterns obtained by the detector. In some embodiments, the data may comprise "image data" from which an image of the target may be reconstructed. The data describing the target may be reconstructed by a processing unit 926 to which the data obtained by the detector is transmitted.

A method for providing illuminating radiation to a target on a surface will now be discussed with reference to FIG. 11. The target may for example be a periodic target positioned on a substrate, such as is used in lithographic processing. In another example, the target is a non-periodic biological structure, such as a cell or other pathological sample.

In a first step 1101, a target on a surface is illuminated with illuminating radiation, the illuminating radiation comprising at least one illuminating radiation beam. Each of the at least one illuminating radiation beams comprise a first illuminating component and a second illuminating component. Each first illuminating component and each corresponding second illuminating component form a periodic illuminating pattern on the surface.

At least one of each of the first and second illuminating components has a controllable characteristic. Examples of controllable characteristics include, but are not limited to, wavelength, phase, incidence angle on the surface, or the optical path length taken by the second illuminating component.

In a second step 1102, the value of the controllable characteristic of each of the first and second illuminating components is controlled. Any suitable number of specific values of the controllable characteristic may be used.

In the present example, the controlling step 1102 is illustrated as occurring after the illuminating step 1101. It is, however, to be noted that this is purely for exemplary purposes and that it should not be interpreted in a limiting fashion. It will be realized that the order of the method steps will, in reality, depend entirely on the specific characteristic being controlled as well as the means by which it is controlled. In certain examples, the illuminating step and the controlling step will occur substantially simultaneously.

A number of specific embodiments of the method described with reference to FIG. 11 may be envisaged by the skilled person. For example, the first and second illuminating components may originate from a single radiation source. In such an example, a radiation source emits first radiation, which is subsequently split into the first and second illuminating components.

In another example, the first and second illuminating components may be emitted by two separate radiation sources. In such an example, the radiation sources are linked so as to ensure that the first and second illuminating component satisfy the coherence requirement, i.e. that they form a periodic illuminating pattern on the surface of the target.

Figure 11:
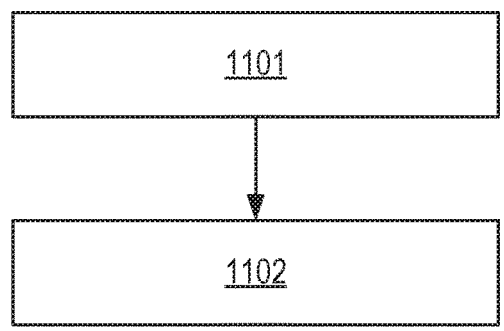
FIG. 11 shows a method for providing illuminating radiation in accordance with a third embodiment of the invention.

The method described in FIG. 11 may be implemented in any suitable apparatus. For example, the method may be implemented in the apparatuses shown in FIGS. 7 and 9.

A specific exemplary apparatus, and corresponding method for acquiring an image of a target on a surface, will now be described with reference to FIGS. 12 and 13. For ease of comparison with FIGS. 7 and 9, elements of FIG. 13 similar to corresponding elements of FIG. 7 or 9 are labelled with reference signs similar to those used in FIG. 7 or 9, but with prefix "11" instead of "7" or "9".

In a first step 1201, a radiation source 1305 is used to provide an illuminating radiation beam 1301. The illuminating radiation beam has a first central wavelength and a first wavelength spectrum. The illuminating radiation beam may have any suitable central wavelength or wavelength spectrum. In one example, the radiation source is a so-called Higher Harmonic Generation (HHG) source. In other examples, the radiation source may be a plasma-discharge source or a free-electron laser.

The radiation source may emit radiation having any suitable wavelength. In the case of the radiation source being a HHG source, the first radiation may have a wavelength between 1 nm and 40 nm. In another example, the radiation source may emit radiation having a wavelength substantially in the visible spectrum. In another example, the radiation source may emit radiation having a wavelength between 400 and 1000 nm.

In a second step 1202, the illuminating radiation beam is split by a beamsplitting component 1303 into a first illuminating component 1302 and a second illuminating component 1304. Since both components originate from the illuminating radiation beam, the first illuminating component and the second illuminating component are mutually coherent immediately after being split. While the present example uses a beamsplitter, alternative embodiments may easily be envisaged wherein the first and second illuminating components live up to the coherence requirement.

In the present example, the third step 1203 of the exemplary method is substantially identical to the first step 1101 of the method of FIG. 11. In the third step, a target 1316 on a surface is illuminated with the first illuminating component and the second illuminating component. In the present example, the first and second illuminating components are directed towards the target by first 1306 and second 1308 optical components (e.g. mirrors) respectively. The first illuminating component and the second illuminating component form a periodic illuminating pattern 1320 on the surface.

In the present example, the fourth step 1204 is substantially identical to the second step 1102 of the method of FIG. 11. In step 1204, the value of the controllable characteristic of the second illuminating component is controlled.

Figure 10:
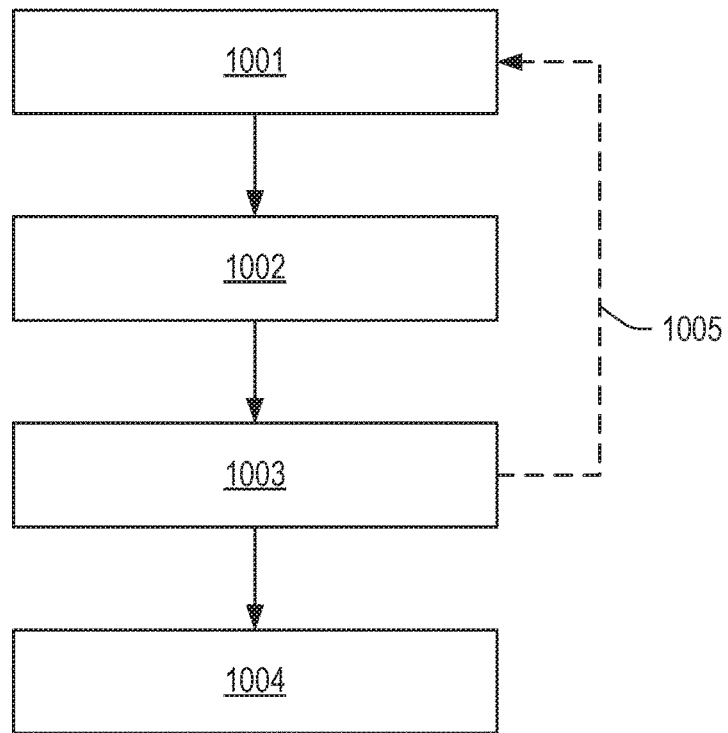
FIG. 10 illustrates a method for using the inspection apparatus of FIG. 9.
Figure 12:
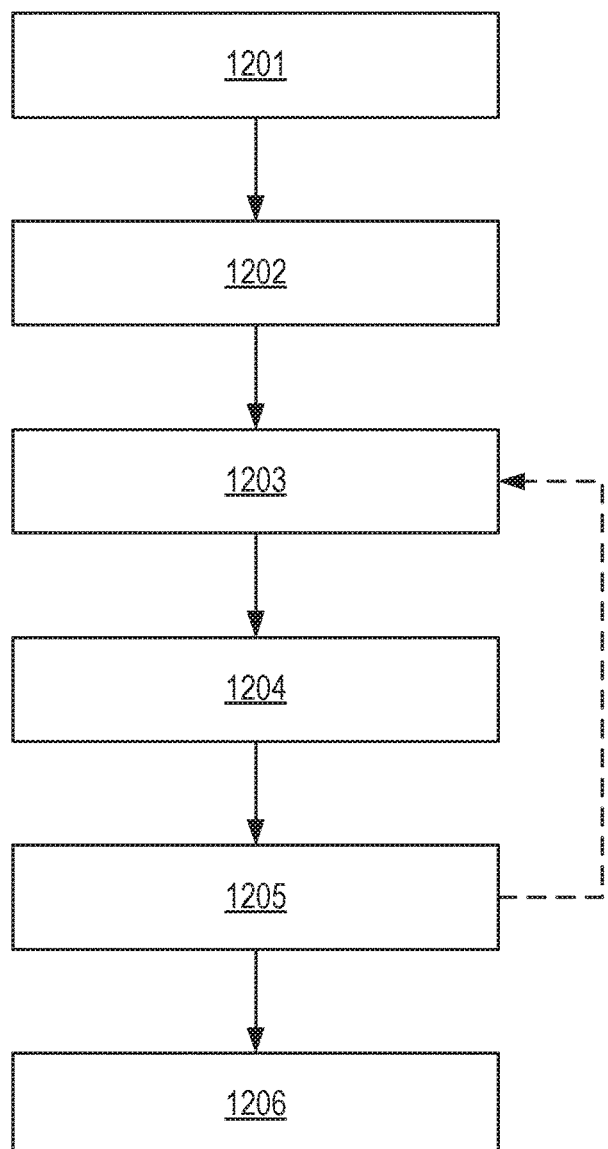
FIG. 12 shows a method for an inspection apparatus in accordance with a fourth embodiment of the invention.
Figure 13:
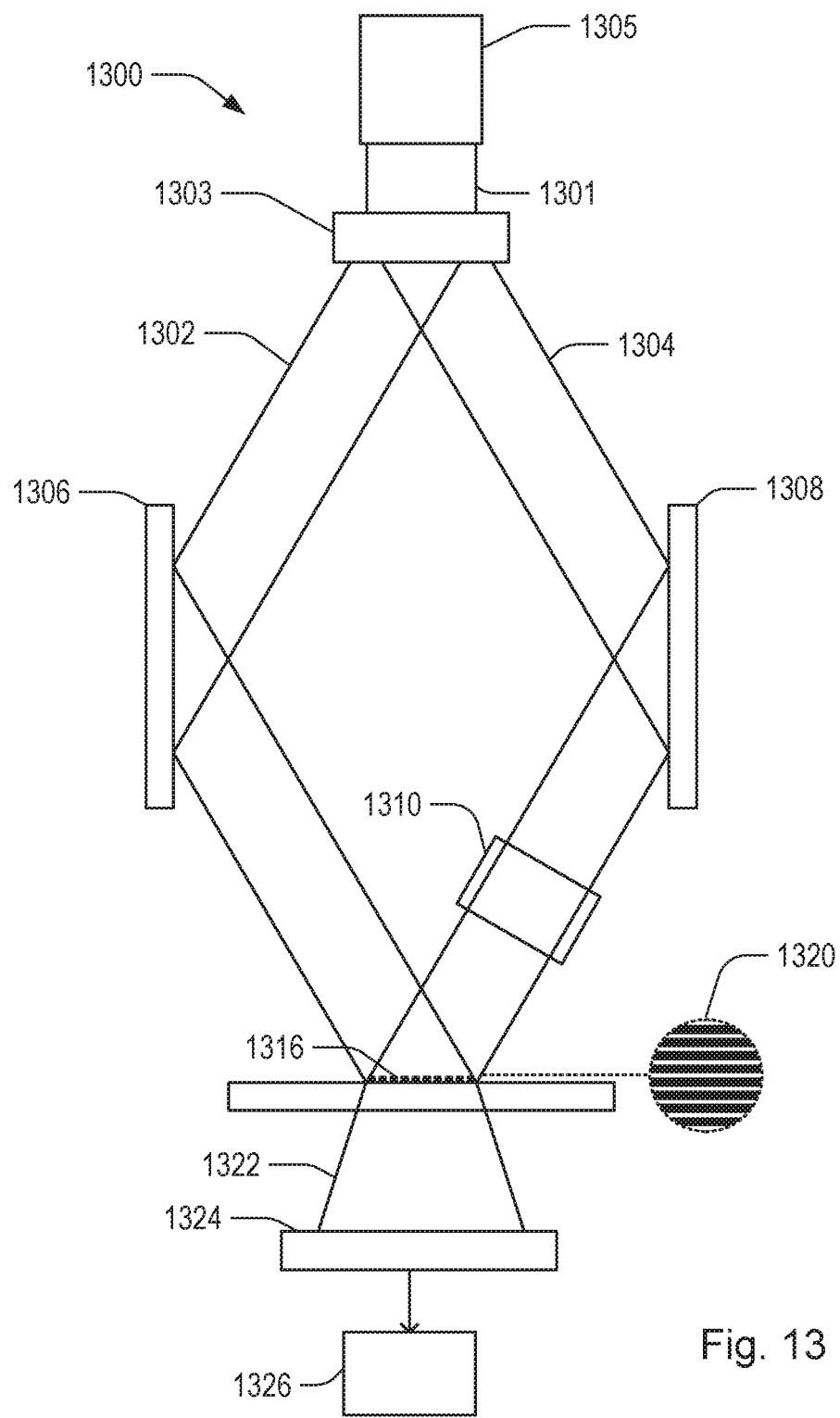
FIG. 13 shows an inspection apparatus in which the method of FIG. 10 may be implemented.

It will of course be noted that the first four steps of the exemplary method 1200 of FIG. 12 also correspond substantially to the providing and illuminating steps of the methods described in FIGS. 8 and 10.

In a fifth step 1205, radiation 1322 scattered by the target is captured at a detector 1324. While the detector is shown in FIG. 13 as receiving radiation transmitted through the target and the surface, it will be appreciated that this is exemplary only. The detector can equally well be positioned so as to receive radiation that is reflected by the target rather than transmitted through the target and the surface (as illustrated in FIG. 13).

The third to fifth steps 1203-1205 may be repeated for a plurality of values of the controllable characteristic in a manner similar to that described with reference to FIG. 10.

In a sixth step 1206, data describing the target is reconstructed based on the data obtained by the detector. In some embodiments, the data may comprise "image data" from which an image of the target may be reconstructed. The data describing the target may be reconstructed by a processing unit 1326 to which the data obtained by the detector is transmitted.

The methods and apparatuses described with respect to FIGS. 9-13 above involve successively capturing a plurality of patterns scattered by a target. It has been realized that, in addition to successively capturing these patterns (which may be referred to as "serial" acquisition), it is possible to capture a plurality of scattered patterns simultaneously (which may be referred to as "parallel" acquisition).

An exemplary apparatus for acquiring an image of a target on a surface based on this realization will now be described with reference to FIG. 14. For ease of comparison with FIG. 13, elements of FIG. 14 similar to corresponding elements of FIG. 13 are labelled with reference signs similar to those used in FIG. 13, but with prefix "14" instead of "13".

The apparatus comprises a plurality of radiation sources 1405a, 1405b, 1405c. Each of the radiation sources emits an illuminating radiation beam 1401a, 1401,b, 1401c having a specific wavelength. In one example, each of the radiation source emits radiation with a wavelength in the visible spectrum (e.g. "blue", "green" and "red" light). The radiation beams propagate to a beamsplitting component 1403, which splits each of the radiation beams into a first illuminating component 1402a, 1402b, 1402c and a second illuminating component 1404a, 1404b, 1404c. Each of the first illuminating components and the corresponding second illuminating components form a periodic illuminating pattern. The target is simultaneously illuminated by a plurality of periodic illuminating patterns 1420a, 1420b, 1420c. In the present example, the first and second illuminating components are directed towards the target by first 1406 and second 1408 optical components (e.g. mirrors) respectively. As each of the illuminating beams have a different radiation wavelength in the present example, each of the periodic illuminating patterns will accordingly have different properties. By controlling the properties of each of the illuminating radiation beams, for example by controlling the radiation sources directly, the properties of the periodic illuminating patterns (e.g. the pitch of the pattern) can be controlled.

The radiation 1422a, 1422b, 1422c scattered by the target is captured at a detector 1424. While the detector is shown in FIG. 14 as receiving radiation transmitted through the target and the surface, it will be appreciated that this is exemplary only. The detector will be positioned so as to receive radiation that is reflected by the target rather than transmitted through the target and the surface (as illustrated in FIG. 3).

Given that the periodic illuminating patterns are not identical, due to the different radiation wavelengths, the periodic illuminating patterns can be used in a manner analogous to the periodic illuminating patterns described in the previous examples. By separating the scattered patterns by appropriate filtering it is possible for the processing unit 1426 to reconstruct the data describing the target.

Figure 14:
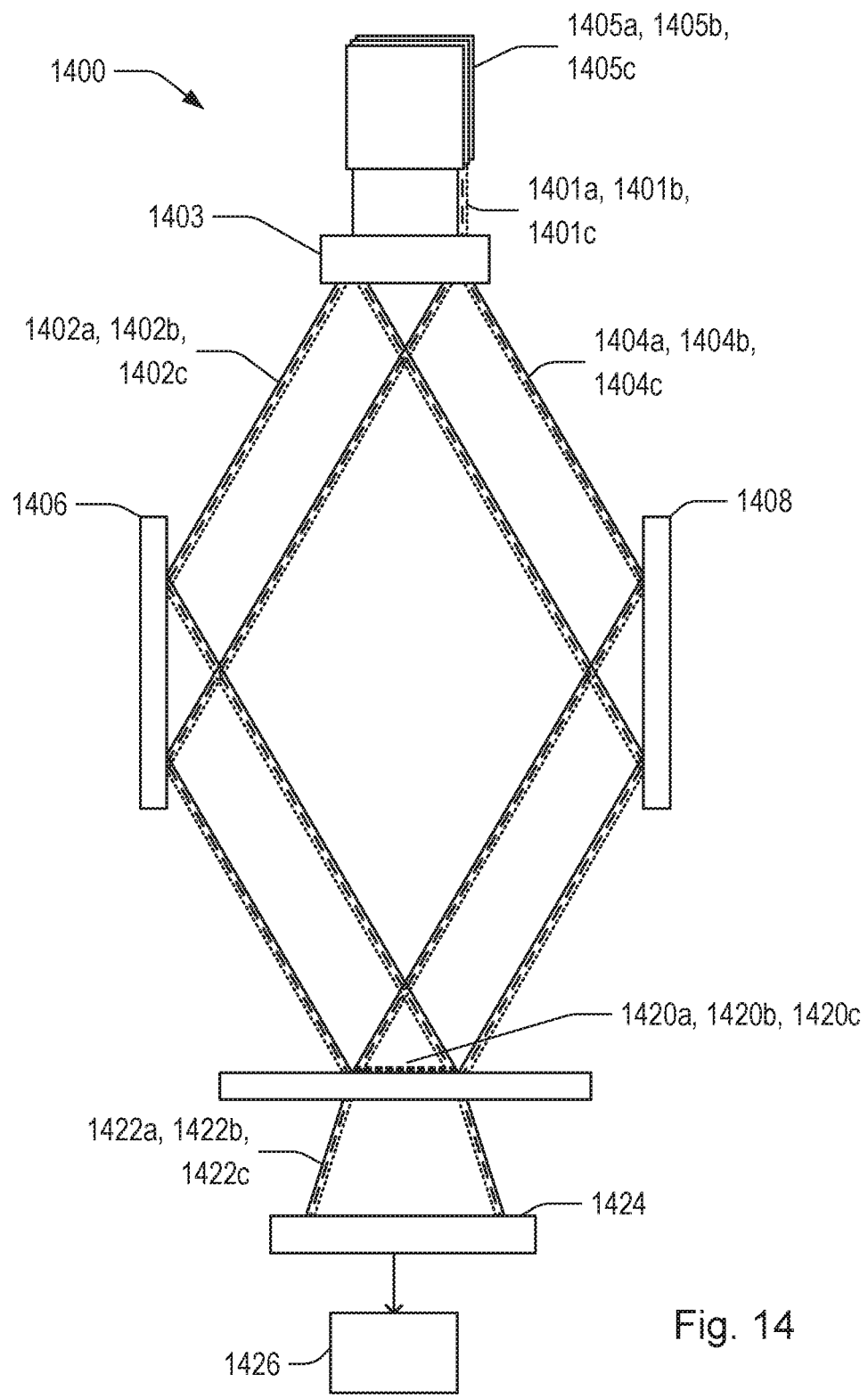
FIG. 14 shows an inspection apparatus according to a fifth embodiment of the invention.

Advantageously, the example of FIG. 14 allows a plurality scattered radiation patterns to be captured simultaneously by a detector, thereby reducing the time required to perform the image capture. Additionally, since all measurements are performed simultaneously, the susceptibility of the measurement to outside influences (e.g. changes in measurement conditions or vibrations in the apparatus) is reduced.

In the examples given above, the targets are shown as periodic targets positioned on surfaces. Periodic targets are commonly placed on substrates used in lithographic processes and are used for making measurements during the lithographic processes. However, as previously described, the above methods and apparatus may equally well be used with non-periodic targets, such as biological structures (e.g. cells or other pathological samples). As such, any specific references lithographic apparatus and methods should be seen as exemplary only and not interpreted in any limiting manner.

Further, it is to be noted that, while the above examples describe apparatuses and methods wherein the radiation propagates through air and using "conventional" optical components (such as mirrors and beamsplitters), many specific implementations may be envisaged by the skilled person. In one example, the apparatus is an all-fiber-based device that uses a fiber-coupled radiation source. Fiber phase shifters are used to control the periodic illumination pattern. In this fashion it is possible to provide an extremely compact, robust and cost-effective apparatus that can provide quantitative phase contrast with micron spatial resolution. The radiation source may in one specific example comprise one or more fiber-coupled laser diodes. In one example, the laser diodes have radiation wavelengths in the near-infrared spectrum for optimal transmission through biological structures. In another example, the laser diodes have radiation wavelengths in the visible spectrum, such as red, green and blue wavelengths, for multi-color imaging of e.g. pathology slides.

It should be noted that, while the above examples has been described as utilizing radiation with a visible wavelength, the principle of the example may be applied to any suitable wavelength range. In one example, the radiation sources emit radiation with EUV wavelengths, and the apparatus comprises a suitable spectrally selective detector.

By the techniques disclosed herein, imaging at high resolution can be performed on real product structures. Comparing with prior knowledge of the nominal structure allows defects to be identified. Prior knowledge may also be used to improve phase retrieval. This may help to reduce the acquisition time and so aid high-volume measurement in high-volume manufacturing context.

In association with the optical system hardware, an implementation of the inspection methods and inspection apparatus disclosed herein may include a computer program containing one or more sequences of machine-readable instructions defining methods of calculating synthetic images and/or controlling the inspection apparatus 400 to implement the illumination modes and other aspects of those metrology recipes. This computer program may be executed for example in a separate computer system employed for the image calculation/control process. Alternatively, the calculation steps may be wholly or partly performed within the processing unit in the apparatus of FIG. 7, 9 or 11 and/or the control unit LACU and/or the supervisory control system SCS of FIGS. 1 and 2. There may also be provided a data storage medium (e.g., semiconductor memory, magnetic or optical disk) having such a computer program stored therein.

Further embodiments according to the present invention are described in below numbered clauses:

1. A method for acquiring data describing a target on a surface, the method comprising:

(i) providing illuminating radiation, wherein the illuminating radiation comprises at least one illuminating radiation beam, and wherein each of the at least one illuminating radiation beams comprises a first illuminating component and a second illuminating component, at least one of each of the first illuminating components or second illuminating components having a controllable characteristic;

(ii) illuminating the target with the at least one illuminating radiation beams such that each first illuminating component and each corresponding second illuminating component form a periodic illuminating pattern;

(iii) capturing at least one scattered radiation pattern formed by the illuminating radiation after scattering by the target for at least one value of the controllable characteristic; and reconstructing data describing the target based on the at least one scattered radiation patterns.

2. A method according to clause 1, wherein the illuminating radiation comprises a first illuminating radiation beam, the second illuminating component of said beam having a controllable characteristic, and wherein the method further comprises repeating steps (i)-(iii) for each of a plurality of values of the controllable characteristic.

3. A method according to clause 2, wherein the controllable characteristic is a phase of the second illuminating component.

4. A method according to clause 2, wherein the controllable characteristic comprises an optical path length of the second illuminating component.

5. A method according to clause 2, wherein the controllable characteristic is an angle of incidence of the second illuminating component relative to the surface.

6. A method according to clause 1, wherein the illuminating radiation comprises a plurality of illuminating radiation beams, the first illuminating component and the second illuminating component of each illuminating radiation beam having a controllable characteristic, and wherein each of the plurality of illuminating radiation beams corresponds to a particular value of the controllable characteristic.

7. A method according to clause 6, wherein the controllable characteristic is a wavelength of the illuminating radiation beam.

8. A method according to any preceding clause, wherein the values for the controllable characteristic are selected from a number of predetermined values.

9. A method according to any preceding clause, comprising using at least three values of the controllable characteristic.

10. A method according to any preceding clause, wherein the illuminating radiation comprises radiation having a wavelength of 400-1100 nm.

11. A method according to any of clauses 1 to 9, wherein the illuminating radiation comprises radiation having a wavelength of 1-40 nm.

12. A method according to any preceding clause, wherein the step of providing comprises:
    using a radiation source to the illuminating radiation; and
    splitting the illuminating radiation to form each of the first illuminating components and the second illuminating components.
13. A method according to clause 12, wherein the step of splitting comprises using a beamsplitter to split the illuminating radiation.
14. A method according to any clauses 1 to 11, wherein the step of providing comprises using a first radiation source to generate each of the at least one first illuminating components and using a second radiation source to generate each of the at least one second illuminating components.
15. A method according to any of clauses 12 to 14, wherein the one or more radiation sources comprises one of the following: a higher harmonic generating (HHG) source; a free electron laser; or a plasma source.
16. A method for illuminating a target on a surface, the method comprising:
    illuminating the target on the surface with illuminating radiation, wherein the illuminating radiation comprises at least one illuminating radiation beam, each of the at least one illuminating radiation beams comprising a first illuminating component and a second illuminating component,
    wherein each of the first illuminating components and each of the corresponding second illuminating components form a periodic illuminating pattern on the target, and
    wherein at least one of each of the first and second illuminating components has a controllable characteristic; and
    controlling the value of the controllable characteristic of each of the at least one first and second illuminating components.
17. A method according to clause 16, wherein the illuminating radiation comprises a first illuminating radiation beam, the second illuminating component of said beam having a controllable characteristic.
18. A method according to clause 17, wherein the controllable characteristic is a phase of the second illuminating component.
19. A method according to clause 17, wherein the controllable characteristic comprises an optical path length of the second illuminating component.
20. A method according to clause 17, wherein the controllable characteristic is an angle of incidence of the second illuminating component relative to the surface.
21. A method according to clause 16, wherein the illuminating radiation comprises a plurality of illuminating radiation beams, the first illuminating component and the second illuminating component of each illuminating radiation beam having a controllable characteristic, and wherein
    each of the plurality of illuminating radiation beams corresponds to a particular value of the controllable characteristic.
22. A method according to clause 21, wherein the controllable characteristic is a wavelength of the illuminating radiation beam.
23. A method according to any of clauses 16 to 22, wherein the values for the controllable characteristic are selected from a number of predetermined values.
24. A method according to any of clauses 16 to 23, comprising using at least three values of the controllable characteristic.
25. A method according to any of clauses 16 to 24, wherein the illuminating radiation comprises radiation having a wavelength of 400-1100 nm.
26. A method according to any of clauses 16 to 24, wherein the illuminating radiation comprises radiation having a wavelength of 1-40 nm.
27. A method according to any of clauses 16 to 26, further comprising steps of:
    using a radiation source to provide the illuminating radiation; and
    splitting the illuminating radiation into each of the at least one first illuminating components and the second illuminating components.
28. A method according to clause 27, wherein the step of splitting comprises using a beamsplitter to split the illuminating radiation.
29. A method according to any of clauses 16 to 26, further comprising a step of using a first radiation source to generate each of the at least one first illuminating components and using a second radiation source to generate each of the at least one second illuminating components.
30. A method according to any of clauses 27 to 29, wherein the radiation source comprises one of the following: a higher harmonic generating (HHG) source; a free electron laser; or a plasma source.
31. An illumination apparatus comprising means for carrying out the method of any of clauses 16 to 30.
32. An inspection apparatus comprising means for carrying out the method of any of clauses 1 to 15.
33. An inspection apparatus according to clause 32, comprising an illumination apparatus according to clause 31.
34. A lithographic apparatus comprising an inspection apparatus according to clause 32 or 33.
35. A method of manufacturing devices wherein device features and metrology targets are formed on a series of substrates by a lithographic process, wherein properties of the metrology targets on one or more processed substrates are measured by a method according to any of clauses 1 to 15, and wherein the measured properties are used to adjust parameters of the lithographic process for the processing of further substrates.
36. A computer program product comprising machine-readable instructions for causing a processor to perform the reconstructing step of any of clauses 1 to 15 or the controlling step of any of clauses 16 to 30.
37. A lithographic system comprising:
    a lithographic apparatus, comprising an illumination optical system arranged to illuminate a pattern, and a projection optical system arranged to project an image of the pattern onto a substrate; and
    an inspection apparatus according to clause 32 or 33,
    wherein the lithographic apparatus is arranged to use one or more parameters calculated by the inspection apparatus in applying the pattern to further substrates.

Although specific reference may have been made above to the use of embodiments of the invention in the context of optical lithography, it will be appreciated that the invention may be used in other applications, for example imprint lithography. In imprint lithography, topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used in relation to the lithographic apparatus encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method for acquiring data describing a target on a surface, the method comprising:
   providing illuminating radiation, wherein the illuminating radiation comprises at least one illuminating radiation beam, wherein the at least one illuminating radiation beam comprises a first illuminating component and a second illuminating component, the second illuminating component having a controllable angle of incidence relative to the surface;
   illuminating the target with at least the first illuminating component and the second illuminating component, the controllable angle of incidence of the second illuminating component is controlled such that the first illuminating component and the second illuminating component of the at least one illumination beam form a periodic illuminating pattern;
   capturing at least one scattered radiation pattern formed by the illuminating radiation after scattering by the target for at least one value of the controllable angle of incidence;
   repeating the providing, the illuminating and the capturing for each of a plurality of values of the controllable angle of incidence; and
   reconstructing the data describing the target based on the at least one scattered radiation patterns.

2. The method of claim 1, wherein the second illuminating component further comprises a controllable phase.

3. The method of claim 1, wherein the second illuminating component further comprises a controllable optical path length.

4. The method of claim 1, wherein the at least one value for the controllable angle of incidence is selected from a number of predetermined values.

5. The method of claim 1, further comprising:
   using at least three values of the controllable angle of incidence.

6. The method of claim 1, wherein the illuminating radiation comprises radiation having a wavelength of 400-1100 nm.

7. The method of claim 1, wherein the illuminating radiation comprises radiation having a wavelength of 1-40 nm.

8. The method of claim 1, wherein the providing comprises:
   using a radiation source to produce the illuminating radiation; and
   splitting the illuminating radiation to form each of the first illuminating component and the second illuminating component.

9. The method of claim 8, wherein the splitting comprises using a beamsplitter.

10. The method of claim 8, wherein the radiation source comprises:
    a higher harmonic generating (HHG) source;
    a free electron laser; or
    a plasma source.

11. The method of claim 1, wherein the providing comprises using a first radiation source to generate the first illuminating component and using a second radiation source to generate the second illuminating component.

12. The method of claim 1, wherein the first illuminating component comprises a controllable characteristic.

13. The method of claim 1, wherein the controllable characteristic of the first illuminating component comprises at least one of wavelength of the first illuminating component, a phase of the first illuminating component, an angle of incidence of the first illuminating component on the surface, or an optical path length of the first illuminating component.

14. A method of manufacturing devices wherein device features and metrology targets are formed on a series of substrates by a lithographic process, wherein properties of the metrology targets on one or more processed substrates are measured by a method comprising:
    using a radiation source to produce illuminating radiation, wherein the radiation source comprises a higher harmonic generating (HHG) source;
    providing the illuminating radiation, wherein the illuminating radiation comprises at least one illuminating radiation beam, and wherein the at least one illuminating radiation beam comprises a first illuminating component and a second illuminating component, at least one of the first illuminating component or the second illuminating component having a controllable characteristic;
    illuminating one of the metrology targets with at least the first illuminating component and the second illuminating component, the controllable characteristic of the at least one of the first illuminating component or the second illuminating component is controlled such that the first illuminating component and the second illuminating component of the at least one illumination beam form a periodic illuminating pattern;
    capturing at least one scattered radiation pattern formed by the illuminating radiation after scattering by the one of the metrology targets for at least one value of the controllable characteristic; and
    reconstructing data describing the one of the metrology targets based on the at least one scattered radiation patterns,
    wherein the measured properties are used to adjust parameters of the lithographic process for the processing of further substrates.

15. The method of claim 14, wherein:
    the illuminating radiation comprises a plurality of illuminating radiation beams, each of the plurality of radiation beams comprises a first illuminating component and a second illuminating component, both the first illuminating component and the second illuminating component of each of the plurality of illuminating radiation beams have the controllable characteristic, and each of the plurality of illuminating radiation beams corresponds to a particular value of the controllable characteristic.

16. The method of claim 15, wherein the controllable characteristic further comprises a wavelength of the plurality of illuminating radiation beams.

17. A method for acquiring data describing a target on a surface, the method comprising:

providing illuminating radiation, wherein the illuminating radiation comprises at least one illuminating radiation beam, and wherein the at least one illuminating radiation beam comprises a first illuminating component and a second illuminating component, the second illuminating component having a controllable angle of incidence relative to the surface;

illuminating the target with at least the first illuminating component and the second illuminating component, the controllable angle of incidence of the second illuminating component is controlled such that the first illuminating component and the second illuminating component of the at least one illumination beam form a periodic illuminating pattern;

capturing at least one scattered radiation pattern formed by the illuminating radiation after scattering by the target for at least one value of the controllable angle of incidence; and using a non-transitory computer program product comprising machine-readable instructions for causing a processor to perform operations reconstructing the data describing the target based on the at least one scattered radiation patterns.

* * * * *